US010758384B2

(12) United States Patent
Yang

(10) Patent No.: US 10,758,384 B2
(45) Date of Patent: Sep. 1, 2020

(54) STENT HAVING REDUCED FORESHORTENING

(71) Applicant: COOK MEDICAL TECHNOLOGIES LLC, Bloomington, IN (US)

(72) Inventor: Shuo Yang, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 225 days.

(21) Appl. No.: 15/208,869

(22) Filed: Jul. 13, 2016

(65) Prior Publication Data
US 2018/0014953 A1 Jan. 18, 2018

(51) Int. Cl.
*A61F 2/06* (2013.01)
*A61F 2/915* (2013.01)
*A61F 2/844* (2013.01)

(52) U.S. Cl.
CPC .............. *A61F 2/915* (2013.01); *A61F 2/844* (2013.01); *A61F 2002/91541* (2013.01); *A61F 2002/91583* (2013.01)

(58) Field of Classification Search
CPC ....................... A61F 2/915; A61F 2/844; A61F 2002/91541; A61F 2002/91583
USPC ................................................ 623/1.11–1.23
See application file for complete search history.

(56) References Cited

U.S. PATENT DOCUMENTS

| | | | | |
|---|---|---|---|---|
| 5,911,754 A * | 6/1999 | Kanesaka | ................. | A61F 2/91 606/198 |
| 5,948,016 A * | 9/1999 | Jang | ........................... | A61F 2/91 623/1.11 |
| 6,042,597 A * | 3/2000 | Kveen | ........................ | A61F 2/91 623/1.15 |
| 6,066,169 A * | 5/2000 | McGuinness | ............. | A61F 2/91 623/1.16 |
| 6,113,627 A * | 9/2000 | Jang | ........................... | A61F 2/91 623/1.49 |
| 6,123,721 A * | 9/2000 | Jang | ........................... | A61F 2/91 623/1.15 |
| 6,200,334 B1 * | 3/2001 | Jang | ........................... | A61F 2/91 606/198 |
| 6,261,319 B1 * | 7/2001 | Kveen | ........................ | A61F 2/91 623/1.15 |
| 6,325,821 B1 * | 12/2001 | Gaschino | ................... | A61F 2/91 606/194 |
| 6,565,598 B1 * | 5/2003 | Lootz | ........................ | A61F 2/91 623/1.15 |

(Continued)

FOREIGN PATENT DOCUMENTS

WO WO 00/62710 A1 10/2000
WO WO 2014/091438 A2 6/2014

OTHER PUBLICATIONS

European Search Report for EP 17275107, dated Dec. 1, 2017, 7 pages.

*Primary Examiner* — Amy R Weisberg
(74) *Attorney, Agent, or Firm* — Brinks Gilson & Lione

(57) ABSTRACT

A stent includes a plurality of stent rings and a plurality of connecting members for connecting adjacent stent rings. The stent rings are expandable from an unexpanded state to an expanded state, each stent ring including a plurality of struts. An adjacent pair of connecting members connected to the same stent ring are disposed to be rotation-symmetric with respect to a center of a strut disposed therebetween.

20 Claims, 11 Drawing Sheets

(56) References Cited

U.S. PATENT DOCUMENTS

| | | | | |
|---|---|---|---|---|
| 8,562,665 B2* | 10/2013 | Jang | ............................ | A61F 2/91 606/195 |
| 8,974,514 B2* | 3/2015 | Anukhin | .................. | A61F 2/915 623/1.15 |
| 9,907,640 B2* | 3/2018 | Seddon | ...................... | A61F 2/04 |
| 2002/0045933 A1* | 4/2002 | Jang | ........................... | A61F 2/91 623/1.15 |
| 2002/0045934 A1* | 4/2002 | Jang | ........................... | A61F 2/91 623/1.15 |
| 2002/0045935 A1* | 4/2002 | Jang | ........................... | A61F 2/91 623/1.16 |
| 2002/0133222 A1* | 9/2002 | Das | ............................ | A61F 2/91 623/1.16 |
| 2003/0014102 A1* | 1/2003 | Hong | ........................ | A61F 2/91 623/1.15 |
| 2004/0133271 A1* | 7/2004 | Jang | ........................... | A61F 2/91 623/1.42 |
| 2004/0172128 A1* | 9/2004 | Hong | ........................ | A61F 2/91 623/1.16 |
| 2007/0173925 A1* | 7/2007 | Fliedner | .................. | A61F 2/856 623/1.15 |
| 2007/0239251 A1* | 10/2007 | Prabhu | ..................... | A61F 2/915 623/1.2 |
| 2009/0036976 A1* | 2/2009 | Beach | ...................... | A61F 2/915 623/1.22 |
| 2010/0204780 A1* | 8/2010 | Fliedner | ..................... | A61F 2/91 623/1.16 |
| 2011/0054592 A1* | 3/2011 | Fliedner | .................. | A61F 2/856 623/1.16 |
| 2011/0071618 A1* | 3/2011 | Baldwin | ................... | A61F 2/88 623/1.16 |
| 2013/0123905 A1* | 5/2013 | Abunassar | ............. | A61F 2/915 623/1.16 |
| 2015/0039072 A1* | 2/2015 | Beach | ..................... | A61F 2/915 623/1.2 |

* cited by examiner

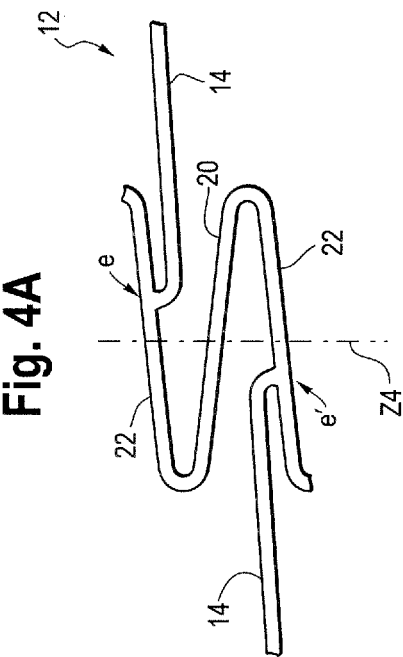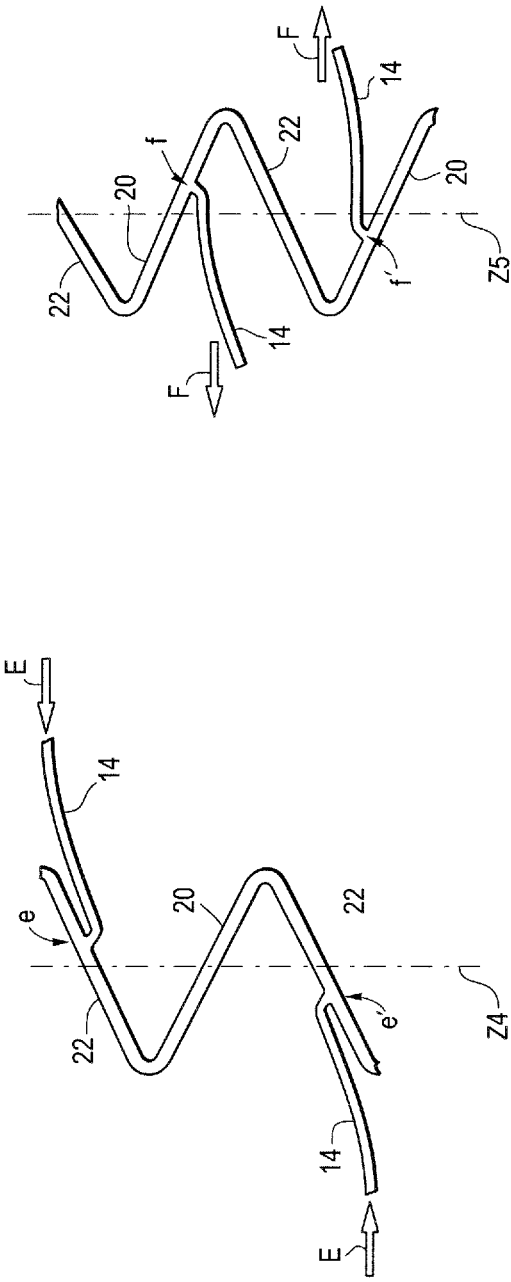

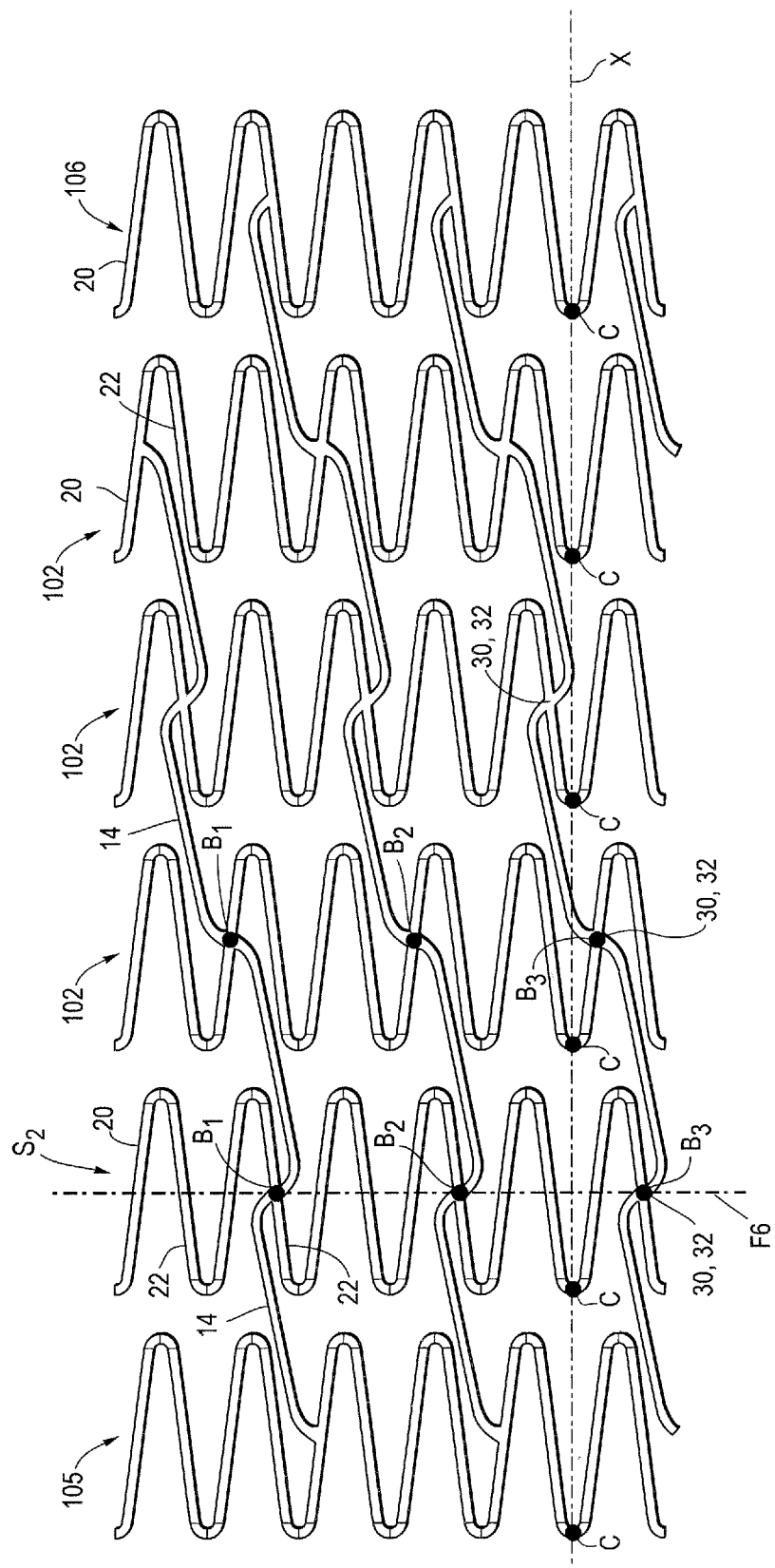

STENT HAVING REDUCED FORESHORTENING

FIELD

The present disclosure relates to medical devices, and more particularly to a prosthesis such as a stent for deployment within a body lumen.

BACKGROUND

The statements in this section merely provide background information related to the present disclosure and may not constitute prior art.

The functional vessels of human and animal bodies, such as blood vessels and ducts, occasionally weaken or even rupture. For example, the aortic wall can weaken, resulting in an aneurysm. One surgical intervention for weakened, aneurismal, or ruptured vessels involves the use of stents or stent grafts to cover the weakened spot in the blood vessel. Stents can be either balloon-expanding (BX) or self-expanding (SX), depending on how the stents are deployed in the body lumen.

The stent, when placed in a body lumen, is subjected to force from blood or other fluid flow. The stent is required to have predetermined radial stiffness, radial strength, and reduced foreshortening to keep the stent in a desired location without being dislodged. Foreshortening refers to the percentage by which the length of a stent decreases from its unexpanded state to its expanded state. It is common for typical stents to experience foreshortening due to radial expansion of the stent. A significant amount of foreshortening of the stent can result in a reduced length of the stent and consequently reduced coverage of the stent against the wall of the lumen.

SUMMARY

In one form of the present disclosure, a stent includes a plurality of stent rings and a plurality of connecting members for connecting adjacent stent rings. The stent rings are expandable from an unexpanded state to an expanded state, each stent ring including a plurality of struts. An adjacent pair of connecting members connected to the same stent ring are disposed to be rotation-symmetric with respect to a center of a strut disposed therebetween.

In another form, a stent includes a plurality of undulating, non-circular stent rings and a plurality of connecting members connecting the stent rings. The stent has a proximal end and a distal end defining a longitudinal direction of the stent. The plurality of stent rings each define a plurality of distal apices. The distal apices of the plurality of stent rings are aligned along a first helical direction defining an angle relative to the longitudinal direction. The connecting members extend along a second helical direction. The second helical direction is different from the first helical direction and the longitudinal direction.

In still another form, a stent includes a plurality of stent rings expandable from an unexpanded state to an expanded state, and a plurality of connecting members for connecting adjacent stent rings. Some of the connecting members are connected to opposite sides of a first stent ring and move toward each other in the longitudinal direction during stent radial expansion. Some of the connecting members are connected to opposite sides of a second stent ring and move away from each other in the longitudinal direction during stent radial expansion to increase the spacing between the second stent ring and an adjacent stent ring. The increased spacing caused by the connecting members connected to the second stent ring compensates for shortening of the first and second stent rings.

Further areas of applicability will become apparent from the description provided herein. It should be understood that the description and specific examples are intended for the purpose of illustration only and are not intended to limit the scope of the present disclosure.

DRAWINGS

In order that the disclosure may be well understood, there will now be described various forms thereof, given by way of example, reference being made to the accompanying drawings, in which:

FIG. 4A is a schematic view of a stent portion in Region A of FIG. 1 in an unexpanded state;

FIG. 4B is a schematic view of a stent portion in Region A of FIG. 1 in an expanded state;

FIG. 5A is a schematic view of a stent portion in Region B of FIG. 1 in an unexpanded state;

FIG. 5B is a schematic view of a stent portion in Region B of FIG. 1 in an expanded state;

FIG. 13 is a schematic view of the pattern of a stent according to a sixth embodiment of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Unless defined otherwise, all technical and scientific terms used herein have the same meaning as commonly understood to one of ordinary skill in the art to which this invention belongs.

The term "stent" means any device or structure that adds rigidity, expansion force or support to a prosthesis. A stent is used to obtain and maintain the patency of a body passageway while maintaining the integrity of the passageway. In addition, the stent may be used to form a seal. The stent may be coated with a polymeric material, for example, by immersion in molten polymer or any other method known to one of skill in the art. The stent may be located on the exterior of the device, the interior of the device, or both. A stent may be self-expanding, balloon-expandable or may have characteristics of both. A variety of other stent configurations are also contemplated by the use of the term "stent." A stent may be attached to a graft to form a "stent graft."

First Embodiment

Figure 1:
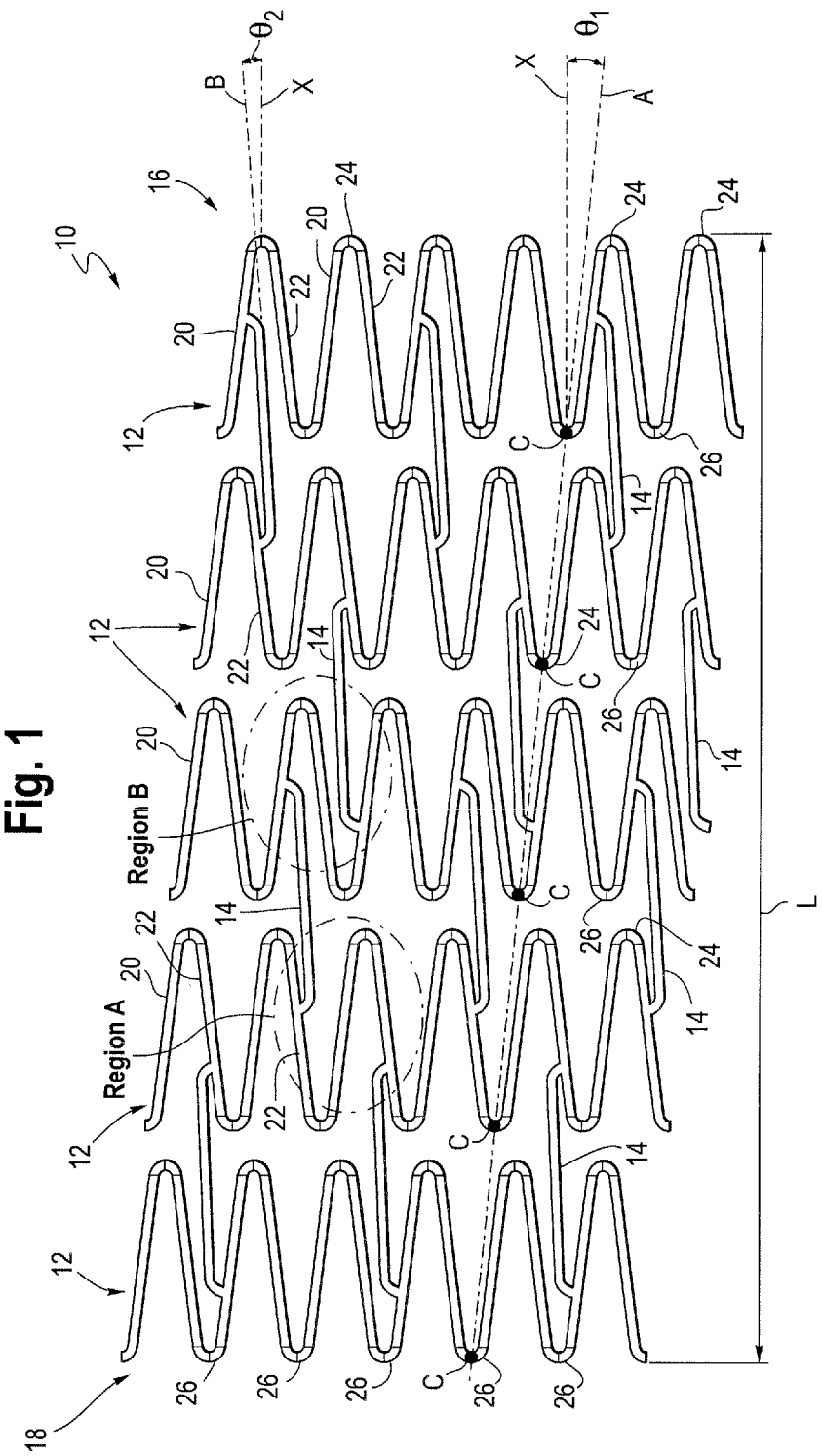
FIG. 1 is a schematic view of the pattern of a stent according to a first embodiment of the present disclosure.

Referring to FIG. 1, a stent 10 according to a first embodiment of the present disclosure includes a plurality of zig-zag rings, or stent rings 12 and a plurality of connecting members 14 connecting the plurality of stent rings 12. The stent 10 defines a proximal end 16 and a distal end 18 which defines a length L of the stent 10 along a longitudinal direction X (i.e., the length direction). The stent rings 12 each define a plurality of proximal apices 24 closer to the proximal end 16 of the stent 10 and a plurality of distal apices 26 closer to the distal end 18 of the stent 10. The proximal apices 24 of adjacent stent rings 12 are aligned along a first helical direction A defining an acute angle $\theta1$ relative to the longitudinal direction X. The distal apices 26 of adjacent stent rings 12 are also aligned along the first helical direction A. In other words, the stent rings 12 are not in phase (peak to valley), nor 180° out of phase (peak to peak). In FIG. 1, some of the distal apices 26 are indicated by reference character C, which define the first helical direction A.

The stent 10 is expandable from an unexpanded state to an expanded state. The stent 10 may include any number of stent rings 12 depending on the size and mechanical properties/nature of the stent 10. The number of stent rings shown in the present embodiment is for illustration only and does not intend to limit the scope of the present disclosure. The diameter of the stent 10 in the expanded state may be determined based upon the diameter of the lumen into which the stent 10 is to be deployed.

The stent rings 12 each include a plurality of first struts 20 and a plurality of second struts 22, which are alternately arranged and connected to define the plurality of proximal apices 24 and the plurality of distal apices 26. The first and second struts 20 and 22 extend in different directions and are connected to form a zig-zag configuration.

The connecting members 14 connect adjacent stent rings 12. The connecting members 14 each have one end connected to a first strut 20 and the other end connected to a second strut 22. The connecting members 14 may be configured to be concave (i.e., disposed below the first and second struts 20 and 22 being connected) or convex (i.e., disposed above the first and second struts 20 and 22 being connected). As shown in FIG. 1, the connecting members 14 connecting the most distal two stent rings 12 are convex, whereas the connecting members 14 connecting the most proximal two stent rings 12 are concave. Sets of the concave and convex connecting members 14 are alternately arranged along the longitudinal direction X. Therefore, the connecting members 14 for connecting the first two stent rings from the distal end 18 are convex. The connecting members 14 for connecting the second and third stent rings from the distal end 18 are concave. The connecting members for connecting the third and fourth stent rings from the distal end 18 are convex, and so on. The connecting members 14 may extend along a second helical direction B, which defines an acute angle $\theta2$ relative to the longitudinal direction X. The second helical direction B is different from the first helical direction A.

The stent rings 12 form the main support structure and provide radial force for the stent 10, whereas the connecting members 14 connect the stent rings 12 together to become an integral structure.

In the present embodiment, the connecting members 14 are not connected to the centers of the struts being connected. The connecting members 14 may have such a length that both ends of the connecting members 14 extend or do not extend beyond the centers of the struts being connected, or only one of the connecting ends of the connecting members 14 extends beyond the center of the strut being connected. In the embodiment of FIG. 1, the concave connecting members 14 overlap a smaller portion of the second struts 22 being connected and do not overlap the centers of the second struts. The concave connecting members 14 overlap a larger portion of the first struts 20 being connected and overlap the centers of the first struts 20 being connected.

Figure 2:
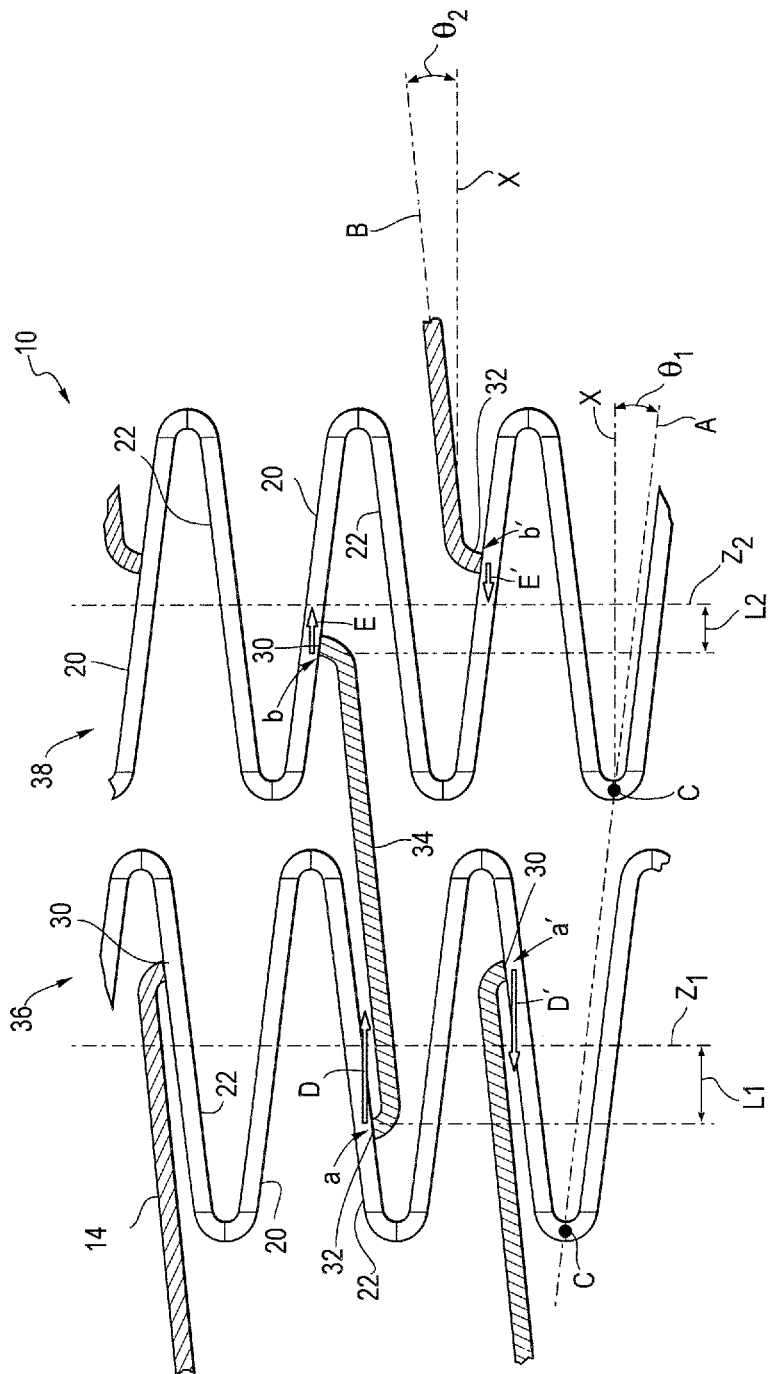
FIG. 2 is an enlarged view a portion of the stent pattern of FIG. 1.

Referring to FIG. 2, each of the connecting members 14 includes a proximal end 30, a distal end 32, and an elongated strut 34 therebetween. The proximal and the distal ends 30, 32 of the connecting members 14 are curved. The elongated struts 34 of the connecting members 14 connect the first strut 20 and second strut 22 in two adjacent stent rings 12 and extend in the second helical direction B.

The plurality of stent rings 12 may include a first stent ring 36 having a first middle axis Z1, and a second stent ring 38 having a second middle axis Z2. The first and second middle axes Z1 and Z2 are perpendicular to the longitudinal direction X. The first middle axis Z1 passes through the centers of the first and second struts 20 and 22 of the first stent ring 36. The second middle axis Z2 passes through the centers of the first and second struts 20 and 22 of the second stent ring 38. The connecting members 14 are connected at their distal ends to only the second struts 22 of the first stent ring 36 and are connected at their proximal ends to only the first struts 20 of the second stent ring 38. The proximal ends 30 and the distal ends 32 of the connecting members 14 are not connected to the centers of the first and second struts 20 and 22 being connected. Instead, the distal ends 32 of the connecting members 14 are offset from the centers of the second struts 22 of the first stent ring 36 (and consequently the first middle axis Z1 of the first stent ring 36) by a first offset distance L1. The proximal ends 30 of the connecting members 14 are offset from the centers of the first struts 20 of the second stent ring 38 (and consequently the second middle axis Z2 of the second stent ring 38) by a second offset distance L2. The first offset distance L1 may be equal to or different from the second offset distance L2. The connecting members 14 cross the first middle axis Z1 of the first stent ring 36 and overlap a larger portion of the second struts 22 being connected. The connecting members 14 do not cross the second middle axis Z2 of the second stent ring 38 and overlap a smaller portion of the first struts 20 being connected. Alternatively, the connecting members 14 may be configured to be shifted toward the proximal end 16 of the stent 10 such that the connecting members 14 cross the second middle axis Z2 (and overlap a larger portion of the first struts 20 being connected) and do not cross the first middle axis Z1 (and overlap a smaller portion of the second struts 22 being connected).

The offset distances L1 and L2 may be "fine-tuned" to achieve a desired foreshortening resistance feature. For example, the first offset distance L1 may be equal to or different from the second offset distance L2. Alternatively, the first and second offset distance L1 and L2 may be set to be zero so that the proximal and distal ends 30, 32 of the connecting members 14 are connected to the centers of the first and second struts 20 and 22 being connected.

When the stent 10 is expanded, the stent rings 12 expand outwardly and increase the angle between the first and second struts 20 and 22. At the same time, the connecting members 14 control and adjust the radial expansion and translational movement of the stent rings 12. When the stent rings 12 radially expand, points a, a' on the first stent ring 36 and points b, b' on the second ring 38 move toward the middle axes Z1 and Z2, respectively. For example, when the first stent ring 36 radially expands, points a and a' on the first stent ring 36 move toward middle axis Z1 as indicated by arrow D and arrow D', respectively. Point a and point a' are disposed on the second struts 20 and are rotation-symmetric relative to the center of the first strut 20 therebetween. As point a and point a' move toward the first middle axis Z1, the connecting members 14 are moved further away in the longitudinal direction X from the first middle axis Z1 of the first stent ring 36. The movement of the connecting members 14 results in an increased spacing between the first stent ring 36 and the adjacent stent ring.

On the other hand, when the second stent ring 38 expands radially, points b and b' on the second stent ring 38 move toward the second middle axis Z2 as indicated by arrow E and arrow E', respectively. As point b and point b' move toward the second middle axis Z2, the connecting members 14 are moved in the longitudinal direction toward the second middle axis Z2. The movement of the connecting members 14 results in a decreased spacing between the second stent ring 36 and the adjacent stent ring. The increased spacing caused by the radial expansion of the first stent ring 36 may compensate for the longitudinal shortening of the first stent ring 36 itself as well as the decreased spacing between the second stent ring 38 and an adjacent stent ring, thereby reducing or eliminating foreshortening. The length compensation mechanism will be better understood with references to FIGS. 4A to 5B, which will be described in more detail below.

Figure 3:
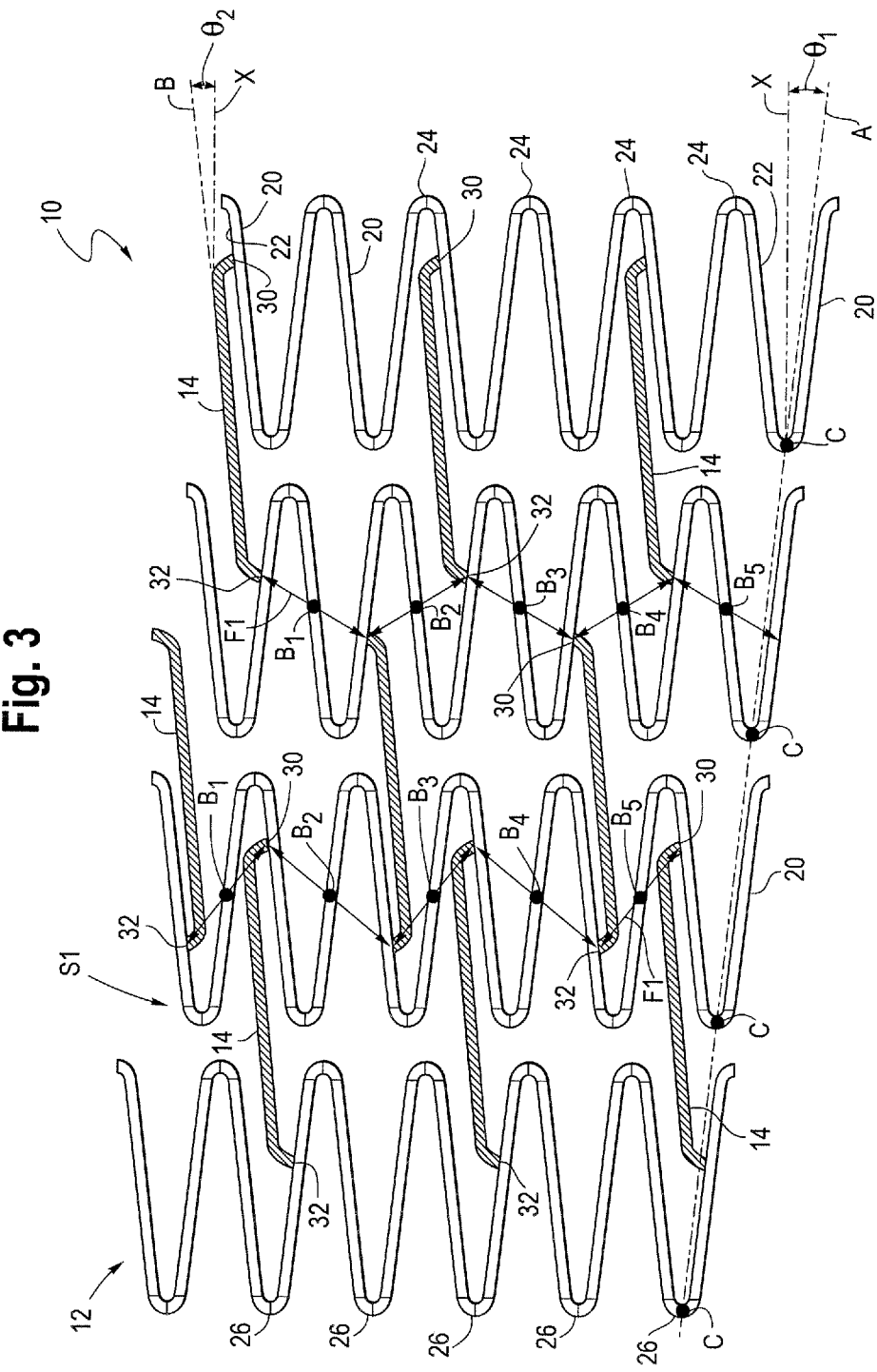
FIG. 3 is a view similar to FIG. 1, showing balance lines and balance centers of the stent rings.

Referring to FIG. 3, the stent 10 has improved foreshortening resistance due to the rotational-symmetric arrangement of the connecting members 14, which result in a plurality of balance centers B1, B2, B3, B4 and B5 in each stent ring 12. The number of balance centers in each stent ring depends on the number of connecting members 14 connected to the stent ring and is not limited to five as shown in FIG. 3.

With respect to a particular stent ring 12, the connecting members 14 are connected to only the first struts 20 or only the second struts 22, regardless of which sides of the particular stent ring 12 the connecting members 14 are connected to. For example, with respect to the stent ring indicated by S1 in FIG. 3, the connecting members 14 are connected to only the second struts 22, regardless of whether the connecting members 14 are also connected to the stent ring on the left, or to the stent ring on the right. For stent ring S1, the first struts 20 are not connected to any connecting members 14. The centers of the first struts 20 become the balance centers B1, B2, B3, B4, and B5.

For this stent ring S1, the proximal ends 30 and the distal ends 32 of the connecting members 14 may be connected to define a balance line F1, which also passes through the balance centers B1, B2, B3, B4, and B5. The balance line F1 in a stent ring constitutes a zig-zag line in the present embodiment. Adjacent pairs of connecting members 14 in this stent ring S1 are rotation-symmetric with respect to a balance center B1, B2, B3, B4, or B5 therebetween.

More specifically, the connecting members 14 immediately above and below the balance center B1 are rotation-symmetric with respect to the balance center B1. The connecting members 14 immediately above and below balance center B2 are rotation-symmetric with respect to balance center B2. The connecting members 14 immediately above and below the balance center B3 are rotation-symmetric with respect to the balance center B3.

Referring to FIGS. 4A, 4B, 5A and 5B, the length compensation mechanism of the stent rings 12 is now explained in more detail. FIGS. 4A and 4B and FIGS. 5A and 5B show the stent portions in Region A and Region B of FIG. 1, respectively. FIG. 4A and FIG. 5A show the stent portions in an unexpanded state, whereas FIGS. 4B and 5B show the stent portions in an expanded state.

As shown in FIGS. 4A and 4B, when the stent ring 12 expands, the connecting ends e and e' move toward the middle axis Z4, and the connecting members 14 move toward the middle axis Z4 as indicated by arrows E due to their connections with the struts of the stent ring 12. The connecting members 14 located at opposite sides of the stent rings 12 are moved in the longitudinal direction X toward each other, thereby moving adjacent stent rings closer to the stent ring 12. As a result, the spacings between the stent ring 12 and adjacent stent rings are decreased. The total longitudinal extent of the stent ring and the connecting members 14 connected thereto, when viewed as a whole, is decreased. The stent ring having this characteristic may be called "a shortening stent ring" because connecting members at opposite sides of the stent rings are moved toward each other to decrease the spacing between the stent ring and the adjacent stent rings.

Referring to FIGS. 5A and 5B, when the stent ring expands radially, the connecting ends f and f' move toward the middle axis Z5, but the connecting members 14 at opposite sides of the stent ring 12 are moved away from each other as indicted by arrows F. The movement of the connecting member 14 causes the spacing between the stent ring and adjacent stent rings to increase. When the stent ring 12 and the connecting members 14 are viewed as a whole, the total longitudinal extent of the stent ring 12 and the connecting members 14 increases. The stent ring having this characteristic may be called "a compensating stent ring" because the connecting members on opposite sides of the stent ring are moved away from either to increase the spacing between the stent ring and an adjacent stent ring, thereby compensating for the longitudinal shortening of the stent ring itself and longitudinal shortening of an adjacent "shortening" stent ring.

Figure 6:
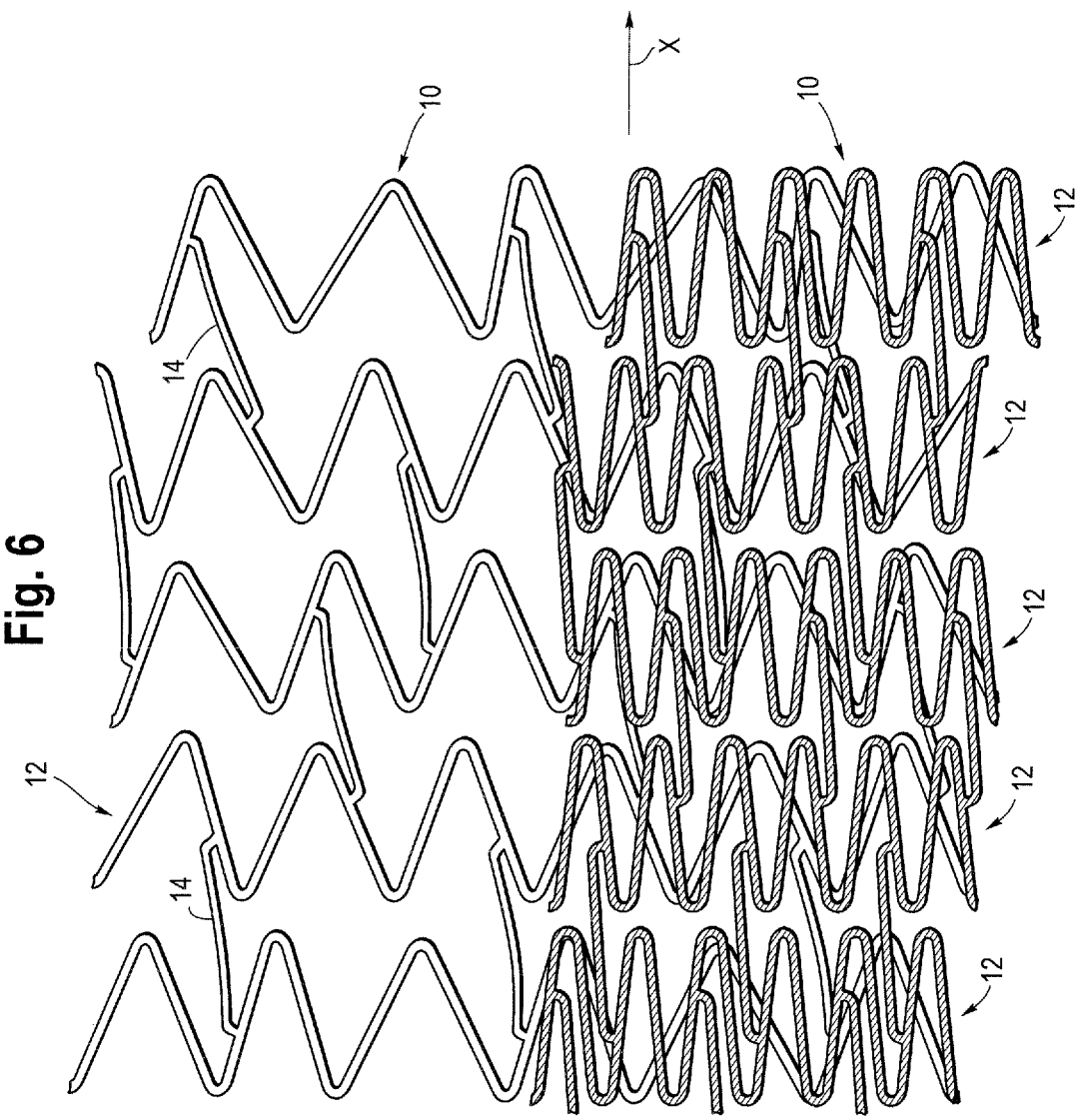
FIG. 6 is a schematic view of an unexpanded stent pattern superimposed on an expanded stent pattern, showing degrees of radial expansion and foreshortening during stent expansion.

FIG. 6 is a schematic diagram of an unexpanded stent superimposed on an expanded stent of the same pattern to show the degree of radial expansion relative to the degree of foreshortening in the longitudinal direction X. The stent 10 includes the "shortening stent rings" and the "compensating stent rings" that are alternately arranged along the longitudinal direction X. A stent ring is a "shortening" or "compensating" stent ring depending on the connecting members that are connected to opposite sides of the stent ring. A stent ring is a shortening stent ring when the connecting members at opposite sides of the stent ring are moved toward each other in the longitudinal direction during stent expansion. A stent ring is a compensating stent ring when the connecting members at opposite sides of the stent ring are moved away from each other in the longitudinal direction during stent expansion. The lengthening effect of the "compensating stent ring" may cancel the shortening effect of an adjacent "shortening stent ring", resulting in a stent having zero or a smaller degree of longitudinal shortening during radial stent expansion.

The adjacent connecting members 14 in the same stent ring 12 define a circumferential spacing. The number of the connecting members 14 in the same stent ring 12 and consequently the circumferential spacing of the connecting members 14 are selected based on a desired flexibility and stability of the stent 10. When the spacing is increased, the number of connecting members 14 is decreased and the flexibility of the stent is increased, resulting in reduced stent radial stiffness per length. When the spacing is decreased and the number of the connecting members 14 is increased, the stent becomes less flexible and has a greater radial stiffness per length. In either case, foreshortening is not affected by the number of connecting members or their circumferential spacings. Foreshortening resistance is maintained due to rotation-symmetric arrangement of the connecting members 14 relative to the balance centers B1, B2, B3, B4, and B5, although the connecting members 14 do not rotate during stent expansion.

The stent 10 can have improved bending flexibility and kink resistance by making the proximal apices or distal apices of the adjacent rings align along a helical direction A to form a helical structure. In the helical structure, the stent rings 12 are neither in phase (peak to valley) nor 180° out of phase (peak to peak). The spaces between two adjacent stent rings 12 where the connecting members 14 are disposed can be increased to accommodate connecting members 14 having different lengths and angles, thereby increasing design flexibility. For example, the connecting members 14 can be configured to extend at a greater angle relative to the longitudinal direction X, or to have greater first and second offset distances L1 and L2.

Figure 7:
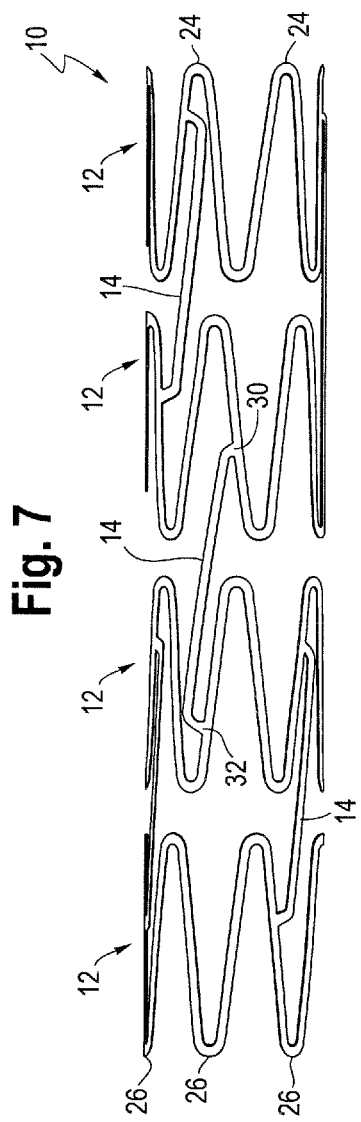
FIG. 7 is a schematic view of the stent of FIG. 1 in an unexpanded state.
Figure 8:
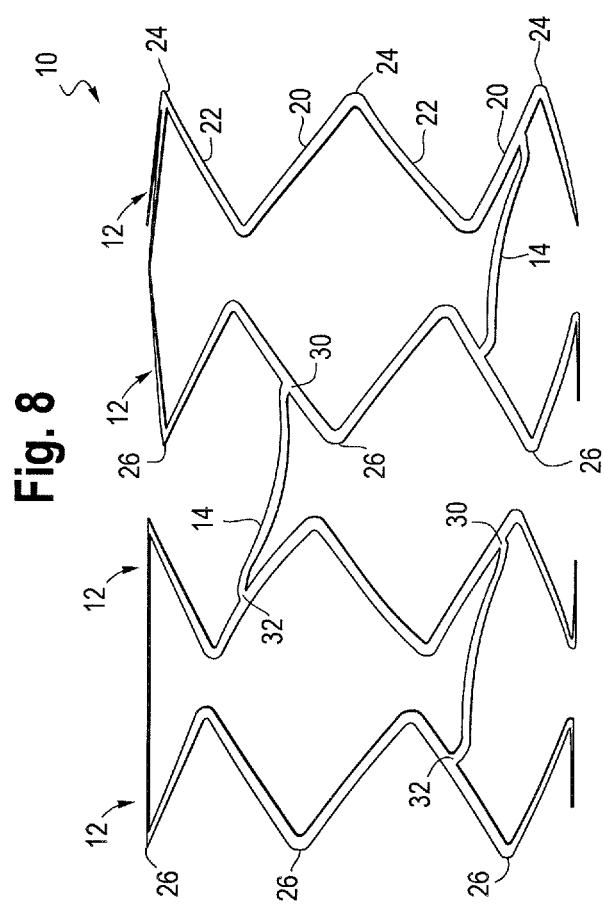
FIG. 8 is a schematic view of the stent of FIG. 1 in an expanded state.

Referring to FIGS. 7 and 8, the stent 10 is shown to be in a radially unexpanded state and a radially expanded state, respectively. The stent 10 may be formed by cutting a cylindrical tube. When the stent 10 is expanded radially as shown in FIG. 5, the stent rings 12 extend outwardly, and the connecting members 14 control and adjust the radial expansion and translational movement of the stent rings 12.

The stent 10 may be formed from biocompatible material. The materials for the stent 10 may be selected from a well-known list of suitable metals. Preferred materials include those materials that can provide the desired functional characteristics with respect to mechanical load bearing, biological compatibility, modulus of elasticity, or other desired properties. In various embodiments, the stent includes a metallic material selected from stainless steel, nickel, silver, platinum, palladium, gold, titanium, tantalum, iridium, tungsten, cobalt, chromium, a nickel-titanium alloy, a superelastic nickel-titanium (NiTi) alloy sold under the trade name NITINOL™ or inconel. Preferably, the individual monolithic stent units are manufactured from nitinol, stainless steel, polymers, or biodegradable materials.

Second Embodiment

Figure 9:
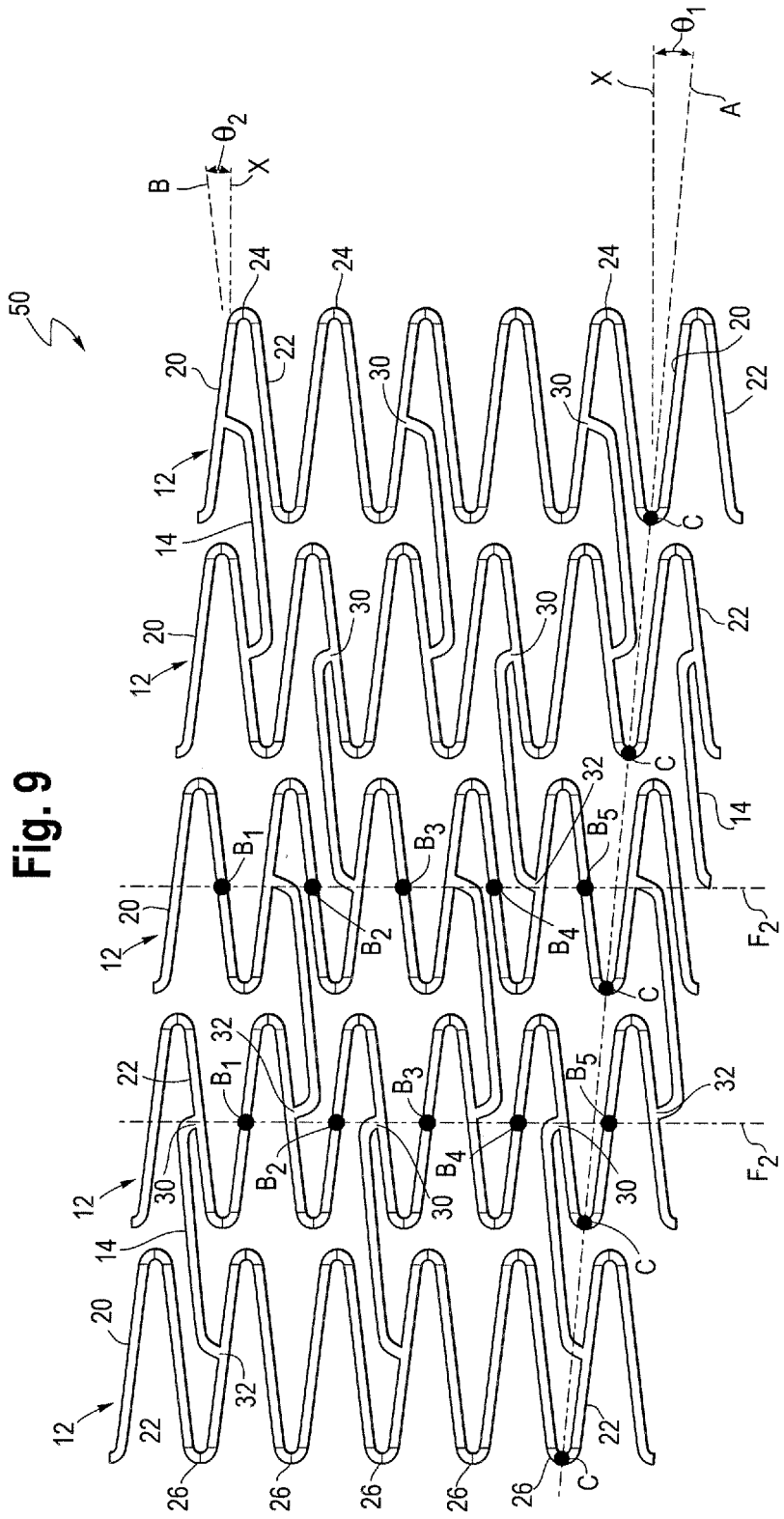
FIG. 9 is a schematic view of the pattern of a stent according to a second embodiment of the present disclosure.

Referring to FIG. 9, a stent 50 according to a second embodiment of the present disclosure has a structure similar to that of the stent 10 in FIG. 1 but differing in the connection between the connecting members and the struts of the stent rings 12. Therefore, similar components are indicated by similar reference numerals and the description thereof is omitted herein for clarity.

The stent 50 includes a plurality of stent rings 12 and a plurality of connecting members 14. Similar to the stent 10 in FIG. 1, the proximal apices or the distal apices of the stent rings 12 are aligned along a first helical direction A, whereas the connecting members 14 extend in a second helical direction B. Unlike the stent 10 of the first embodiment, the connecting members 14 are connected to the centers of the first and second struts 20 and 22 of the stent rings 12. In other words, the first and second offset distances L1 and L2 as shown in FIG. 2 are set to be zero. Each stent ring 12 defines balance centers B1, B2, B3, B4 and B5, which are the centers of the struts on which no connecting member is connected. The balance line F2 that connects the proximal ends 30 and the distal ends 32 of the connecting members 14 is a straight line and also passes through the balance centers B1, B2, B3, B4 and B5. In a broad sense, the connecting members 14 are arranged to be rotation-symmetric with respect to the balance centers B1, B2, B3, B4 and B5, although the connecting members 14 do not rotate during stent expansion. When the stent rings 12 expand radially, the angle of the struts 20, 22 of the stent rings 12 increases and the connecting ends of the connecting members 14 move along the middle axes F2 of the stent rings 12. The adjacent stent rings 12 have the same amount of radial expansion. Therefore, the connecting members 14 undergo translational movement along a direction parallel to the middle axes F2 of the stent rings 12 during stent radial expansion. No or very little foreshortening occurs in the stent 50 of this embodiment.

Third Embodiment

Figure 10:
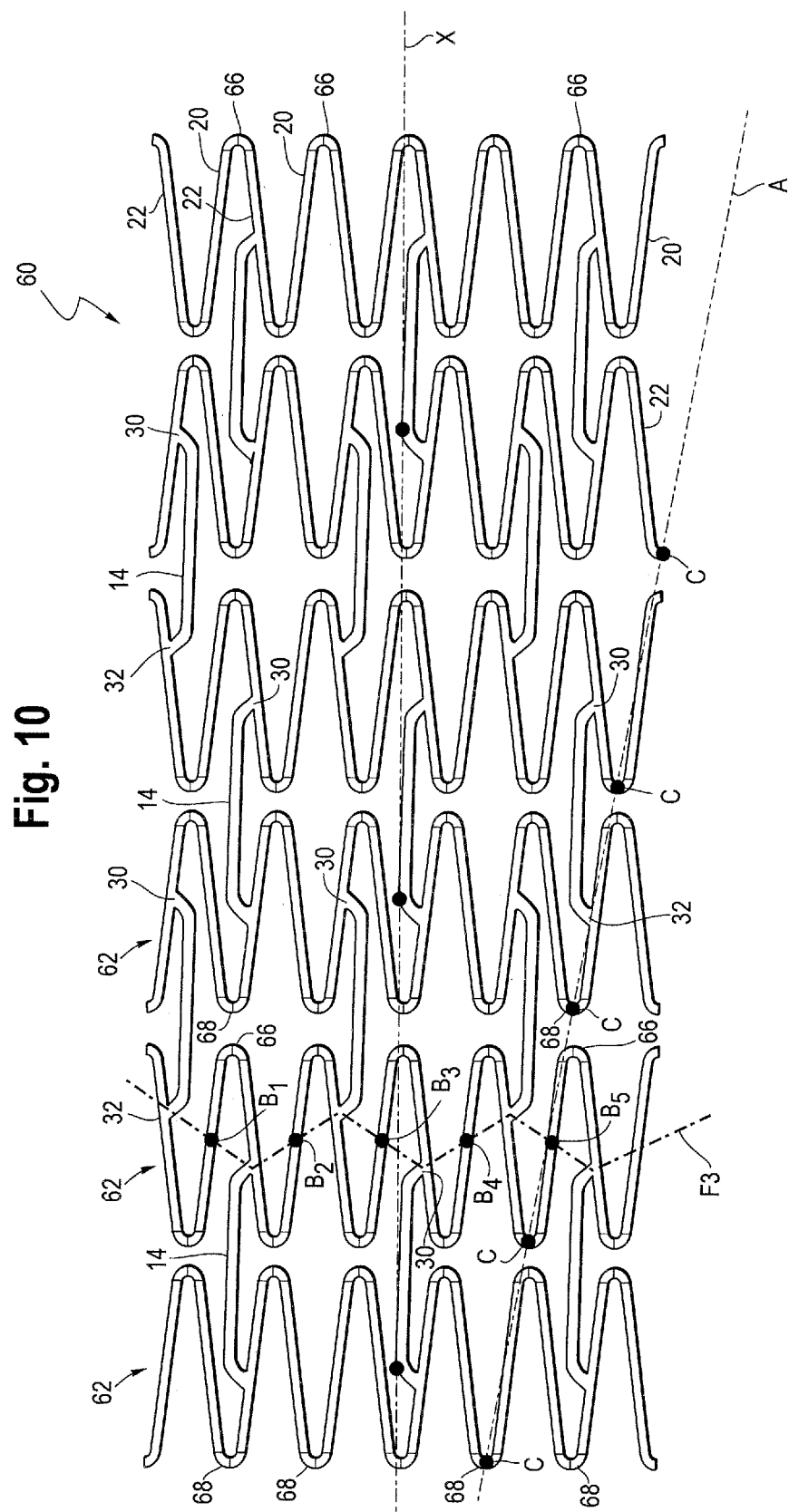
FIG. 10 is a schematic view of the pattern of a stent according to a third embodiment of the present disclosure.

Referring to FIG. 10, a stent 60 according to a third embodiment of the present disclosure includes structure similar to that of the stent 10 in FIG. 1 except that a plurality of stent rings 62 are aligned along the longitudinal direction X, rather than aligned along a first helical direction A.

More specifically, the stent 60 includes a plurality of stent rings 62 and a plurality of connecting members 14. The stent rings 62 each include proximal apices 66 and distal apices 68. The proximal apices 66 of one stent ring 62 face the distal apices 68 of an adjacent stent ring 62. In other words, the stent rings 62 are arranged 180° out of phase in a peak to peak configuration. The proximal apices 66 and the distal apices 68 of the stent rings 62 are aligned along the longitudinal direction X. The connecting members 14 are offset from the centers of the first and second struts 20 and 22 of the stent rings 62. As a result, the proximal ends 30 and the distal ends 32 of the connecting members 14 for each stent ring 62 define a zig-zag balance line F3, which also passes through the centers of the struts not being connected. The centers of the struts not being connected to any connecting members 14 become balance centers B1, B2, B3, B4, and B5. For each stent ring 62, two adjacent connecting members 14 are rotation-symmetric with respect to the balance centers B1, B2, B3, B4 and B5. Moreover, the connecting members 14 are not connected to the centers of the struts being connected. The connecting members 14 overlap a larger portion of the first struts 20 being connected and overlap a smaller portion of the second struts 22 being connected for all stent rings 62. Therefore, the connecting members 14 are not connected to the struts of the adjacent stent rings 62 at the same height and thus extend in a direction defining an acute angle relative to the longitudinal direction X.

Although the stent 60 does not have a helical structure (where the proximal apices or the distal apices of the stent rings are aligned along a helical direction) as described above, the rotation-symmetric arrangement of the connecting members 14 relative to the balance centers B1, B2, B3, B4 and B5 allows the stent 60 to have improved foreshortening resistance. As previously described in connection with FIGS. 4A, 4B, 5A and 5B, when the stent rings 62 expand, the connecting ends of the connecting members 14 are moved toward the middle axes F3 of the stent rings to which they are connected. The connecting members 14 connected to opposite sides of one stent ring 62 move closer to each other in the longitudinal direction X, whereas the connecting members 14 connected to opposite sides of another stent ring 62 move away from each other in the longitudinal direction X to thereby increase the spacing between the another stent ring and an adjacent stent ring. Therefore, the shortening of the one stent ring may be compensated by the increased spacing caused by the connecting members connected to the another stent ring. The compensating mechanism has been described in connection with FIGS. 4A, 4B, 5A and 5B and thus the detailed description thereof is omitted for clarity.

Fourth Embodiment

Figure 11:
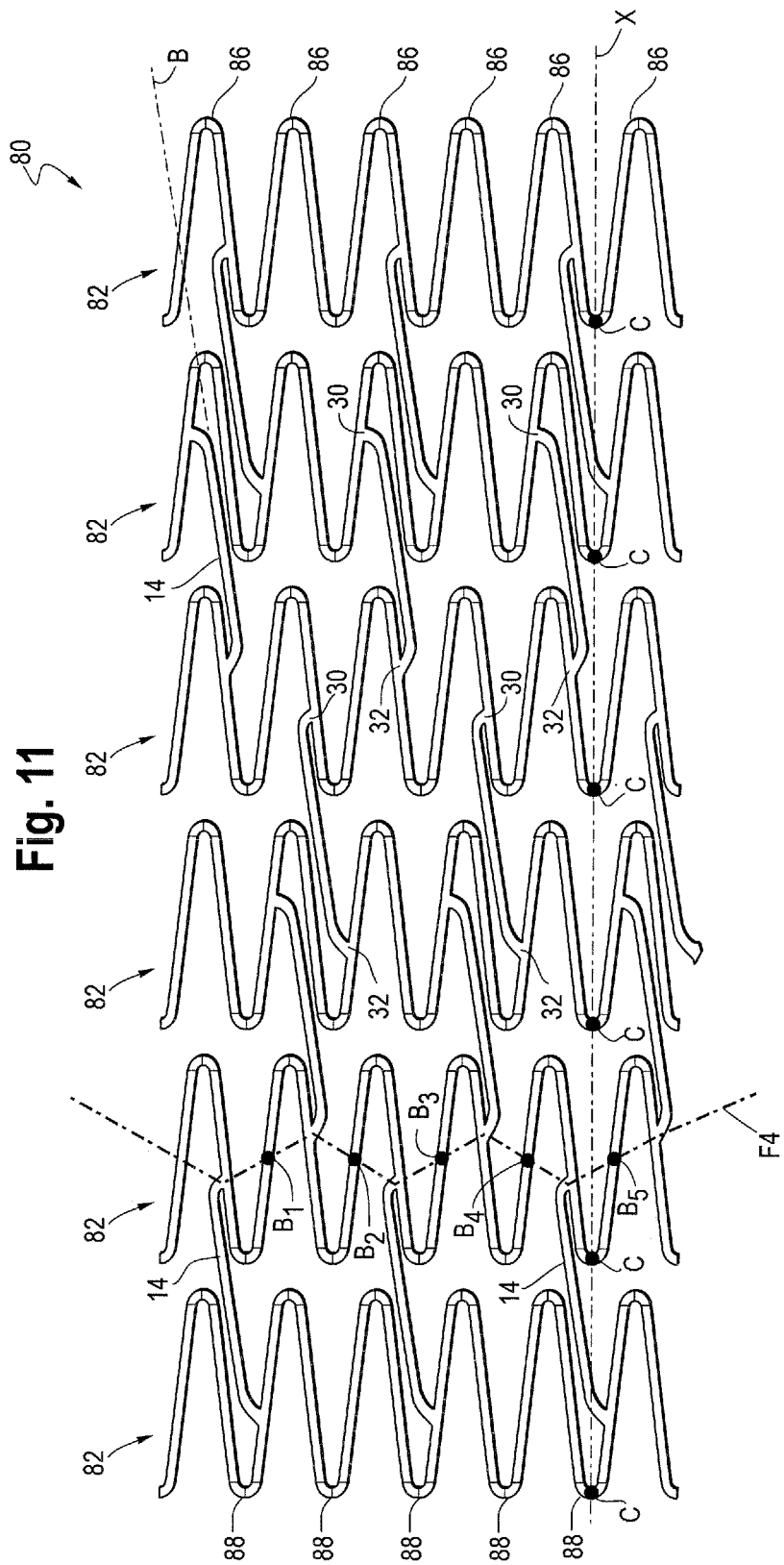
FIG. 11 is a schematic view of the pattern of a stent according to a fourth embodiment of the present disclosure.

Referring to FIG. 11, a stent 80 according to a fourth embodiment of the present disclosure includes a structure similar to that of the stent 10 of the first embodiment except that the stent rings are aligned. More specifically, the stent 80 includes a plurality of stent rings 82 and a plurality of connecting members 14. The stent rings 82 each define proximal apices 86 and distal apices 88. The proximal apices 86 of the stent rings 82 are aligned along the longitudinal direction X. The distal apices 88 of the stent rings 82 are aligned along the longitudinal direction X. In other words, the stent rings 12 are arranged in phase in a peak to valley configuration. Only the connecting members 14 are helically arranged and extend along the second helical direction B. The proximal ends 30 and the distal ends 32 of the connecting members 14 are offset from the centers of the struts being connected. Therefore, the balance line F4 that connects the proximal ends 30 and the distal ends 32 of the connecting members 14 for a particular stent ring 82 constitutes a zig-zag line. As in any of the preceding embodiments, the connecting members 14 are rotation-symmetric with respect to the balance centers B1, B2, B3, B4, B5, which are centers of the struts not being connected to any connecting members 14.

Although the stent 80 does not have a helical structure, the rotation-symmetric arrangement of the connecting members 14 relative to the balance centers B1, B2, B3, B4 and B5 allows the connecting members connected to a particular stent ring to increase the spacings between the particular stent ring and adjacent stent rings, similar to that described in connection with FIGS. 5A and 5B. The increased spacings by the connecting members connected to the particular stent ring may compensate for the shortening of an adjacent stent ring which undergoes foreshortening according to FIGS. 4A and 4B. The compensating mechanism has been described in connection with FIGS. 4A, 4B, 5A and 5B and thus the detailed description thereof is omitted for clarity.

Fifth Embodiment

Figure 12:
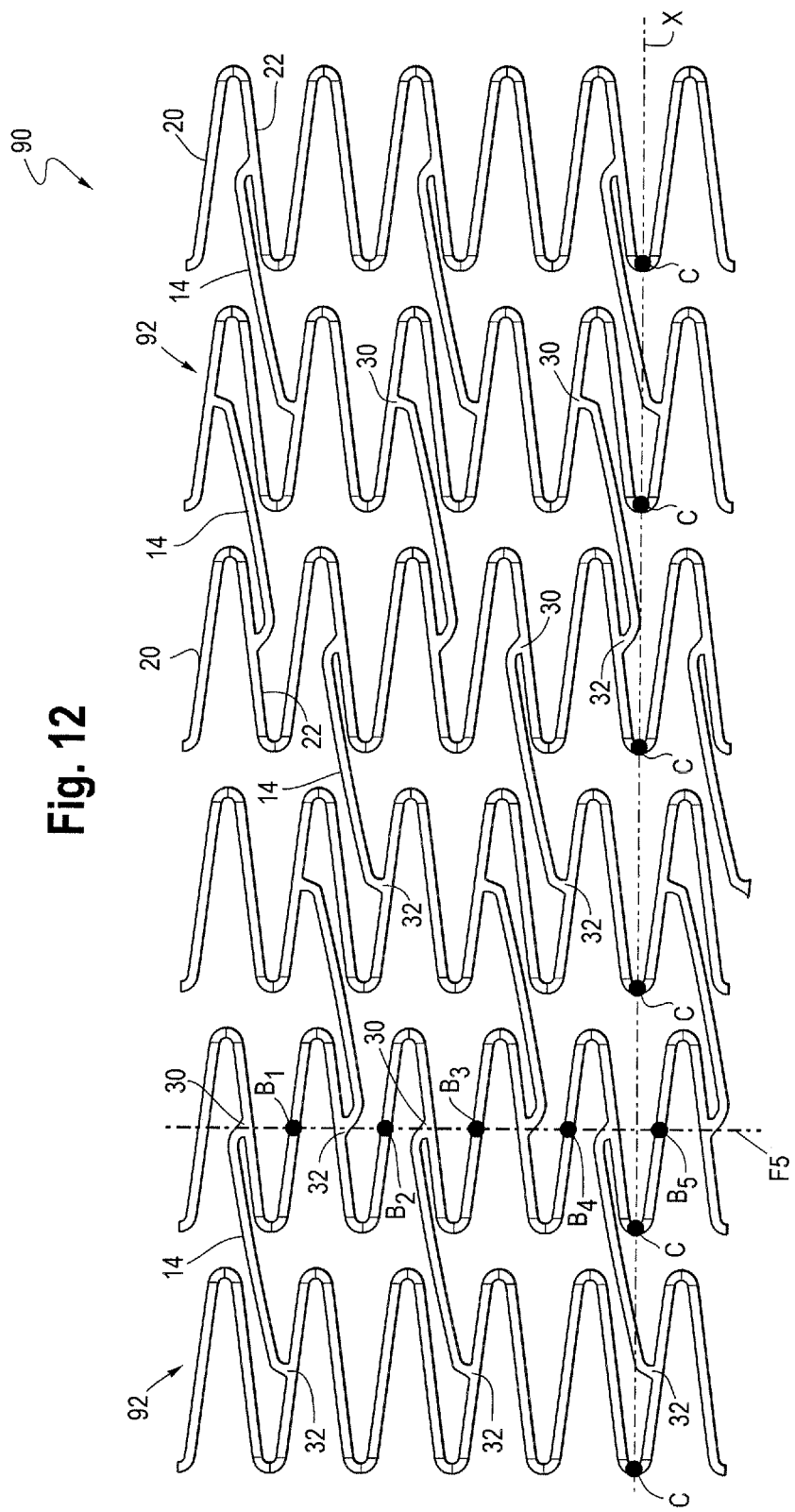
FIG. 12 is a schematic view of the pattern of a stent according to a fifth embodiment of the present disclosure.

Referring to FIG. 12, a stent according to a fifth embodiment of the present disclosure is structurally similar to that of the stent 80 of FIG. 11, but differing only in the connection locations of connecting members 14 to the stent rings. In the present embodiment, the connecting members 14 are connected to centers of the first and second struts 20 and 22 being connected. Therefore, for a particular stent ring 92, the balance line F5 that connects the proximal ends 30 and the distal ends 32 of the connecting members 14 constitutes a straight line. In a broad sense, the adjacent connecting members 94 are disposed to be rotation-symmetric with respect to a balance center B1, B2, B3, B4 or B5 therebetween. When the stent rings 92 expand radially, the angle of the struts 20, 22 of the stent rings 92 increases and the connecting ends of the connecting members 14 move along the middle axis F5 of the stent rings 92. The adjacent stent rings 92 have the same amount of radial expansion. Therefore, the connecting members 14 undergo translational movement along a direction parallel to the middle axis F5 of the stent rings 92 during stent radial expansion. No or very little foreshortening occurs in the stent 90 of this embodiment.

Sixth Embodiment

Referring to FIG. 13, a stent 100 according to a sixth embodiment of the present disclosure is structurally similar to that of the stent of FIG. 12, except for the arrangement of the connecting members. The stent 100 includes a plurality of stent rings 102 and a plurality of connecting members 14.

The connecting members 14 are connected to centers of the first and second struts 20 and 22 of the stent rings 102. In addition, two adjacent connecting members 14 are connected to the same first strut 20 or the same second strut 22. As shown in FIG. 13, for the particular stent ring indicated by S2, the upper two connecting members 14 are connected to the same second strut 22, the middle two connecting members 14 are connected to the same second strut 22, and the lower two connecting members 14 are connected to the same second strut 22. Therefore, the connecting members 14 are interconnected through the first struts 20 or the second struts 22 to form a continuous connecting assembly extending from a distal stent ring 105 to a proximal stent ring 106. Unlike the balance centers in the previous embodiments, which are the centers of the struts not connected to any connecting members 14, the balance centers B1, B2 and B3 in the present embodiment are the centers of the first or second struts being connected. Similarly, the adjacent connecting members 14 are arranged to be rotation-symmetric with respect to the balance centers B1, B2, B3 in a broad sense, although no rotation of the connecting members 14 occurs during stent expansion. Sets of the concave and convex connecting members 14 are alternately arranged along the longitudinal direction. When the stent rings 102 expand radially, the angle of the struts 20, 22 of the stent rings 102 increases and the connecting ends of the connecting members 14 move along the middle axes F6 of the stent rings 102. The adjacent stent rings 102 have the same amount of radial expansion. Therefore, the connecting members 14 undergo translational movement along a direction parallel to the middle axes F6 during stent radial expansion. No or very little foreshortening occurs in the stent 100 of this embodiment.

In any of the present embodiments, the stent 10, 50, 60, 80, 90, 100 has a plurality of connecting members 14 arranged in a rotation-symmetric relationship relative to the balance centers B1, B2, B3, B4, B5 although no rotation of the connecting members actually occurs. The concave connecting members and the convex connecting members are alternately arranged along the longitudinal direction X. Therefore, in some embodiments where the connecting members are not connected to the centers of the struts being connected, the connecting members at opposite sides of some of the stent rings move away from each other in the longitudinal direction during stent expansion to increase the spacings between the stent rings. As such, the shortening of the stent ring itself or the shortening of an adjacent stent ring is canceled by or compensated by the increased spacings by the connecting members during stent radial expansion. In other embodiments where the connecting members are connected to the centers of the struts being connected, the connecting ends of the connecting members move along the middle axes of the stent rings and the connecting members undergo only translational movement in a direction parallel to the middle axes of the stent rings. The spacings between adjacent stent rings are not changed and thus no foreshortening occurs during stent expansion.

It is understood that the stents 10, 50, 60, 80, 90, 100 described in any of the embodiments may be attached to a graft material to a form stent graft or be attached to any conventional components to form an endoluminal device.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A stent comprising:
   a plurality of stent rings expandable from an unexpanded state to an expanded state and each including a plurality of struts; and
   a plurality of connecting members for connecting adjacent stent rings,
   wherein an adjacent pair of connecting members connected to the same stent ring each have one end connected to the same stent ring and the other end connected to an adjacent stent ring,
   wherein the adjacent pair of connecting members are disposed at opposite sides of the same stent ring along the longitudinal direction,
   wherein the connecting members connected to two adjacent stent rings each have one end crossing a center of the strut being connected and overlapping a larger portion of the strut being connected, and the other end not crossing a center of the strut being connected and overlapping a smaller portion of the strut being connected, and
   wherein the ends of circumferentially adjacent connecting members that connect to struts in a particular stent ring lie on a line that passes through the center of the strut between the connecting members, and extend in a direction defining a non-parallel angle relative to a longitudinal direction of the stent.

2. The stent according to claim 1, wherein one of the adjacent pair of connecting members defines a concave shape, and the other one of the adjacent pair of connecting members defines a convex shape.

3. The stent according to claim 1, wherein the strut disposed between the adjacent pair of connecting members is not connected to any connecting member.

4. The stent according to claim 1, wherein the stent rings each include a plurality of proximal apices, the plurality of proximal apices of the stent rings being aligned along a first helical direction.

5. The stent according to claim 1, wherein connecting points at which the connecting members are connected to a stent ring define a zig-zag line.

6. The stent according to claim 5, wherein the zig zag line passes through centers of struts of the stent ring not connected to any connecting member.

7. The stent ring according to claim 1, wherein the connecting members each define a curved proximal end, a curved distal end, and an elongated strut therebetween.

8. The stent ring according to claim 7, wherein the elongated struts of the connecting members are parallel to some of the struts of the stent rings.

9. A stent including a proximal end and a distal end, the proximal end and the distal end defining a longitudinal direction, the stent comprising:
   a plurality of stent rings, each stent ring defining a plurality of distal apices; and
   a plurality of connecting members connecting the stent rings,
   wherein the distal apices of the plurality of stent rings are aligned along a first helical direction defining an acute angle relative to the longitudinal axis, the connecting members extending along a second helical direction defining an acute angle relative to the longitudinal direction, the second helical direction being different from the first helical direction and the longitudinal direction,
   wherein each of the stent rings are not in phase or 180 degrees out of phase,
   wherein the stent rings each include a plurality of struts connected at their ends to define a zig-zag ring,
   wherein two adjacent connecting members for each stent ring are connected to the struts at locations such that the ends of circumferentially adjacent connecting members that connect to struts in a particular stent ring lie on a line that passes through the center of the strut between the connecting members, and
   wherein the two adjacent connecting members are spaced apart by a strut not connected to any connecting member.

10. The stent according to claim 9, wherein the first helical direction and the longitudinal direction define an acute angle.

11. The stent according to claim 9, wherein the stent rings each include a plurality of struts connected at their ends to define a zig-zag ring.

12. The stent according to claim 11, wherein the connecting members are connected to some of the plurality of struts at locations offset from centers of the struts being connected.

13. The stent according to claim 9, wherein the adjacent connecting members are connected to different struts of the stent ring.

14. The stent according to claim 9, wherein the adjacent connecting members are connected to the same strut of the stent ring.

15. A stent comprising:
   a plurality of stent rings expandable from an unexpanded state to an expanded state and each including a plurality of struts connected to define a plurality of distal and proximal apices, the plurality of stent rings including a first stent ring, a second stent ring, and a third stent ring, wherein the first, second and third stent rings are adjacent to one another, the second stent ring disposed between the first stent ring and the third stent ring; and
   a plurality of connecting members for connecting adjacent stent rings at points away from the distal and proximal apices, wherein the connecting members connected to the second stent ring each have one end connected to the second stent ring and the other end connected to one of the first and third stent rings, wherein in the expanded state the connecting members connected to both the second stent ring and the first stent ring move away from the connecting members connected to both the second stent ring and the third stent ring in a longitudinal direction during stent radial expansion, wherein the first, second and third stent rings each include a plurality of struts, the connecting members being connected to the struts at points offset from centers of the struts of the first, second and third stent rings being connected, and wherein the connecting members connected to the first stent ring do not cross a middle axis of the first stent ring, the middle axis of the first stent ring passing through centers of the struts of the first stent ring, and wherein the connecting members connected to the second stent ring cross a middle axis of the second stent ring, the middle axis of the second stent ring passing through centers of the struts of the second stent ring.

16. The stent according to claim 15, wherein the connecting members connected to the first stent ring each overlap a portion of the strut of the first stent ring being connected, the portion being larger than a half of a length of the strut of the first stent ring being connected.

17. The stent according to claim 15, wherein the connecting members connected to the third stent ring do not cross a middle axis of the third stent ring, the middle axis of the third stent ring passing through centers of the struts of the third stent ring.

18. A stent including a proximal end and a distal end, the proximal end and the distal end defining a longitudinal direction, the stent comprising:
  a plurality of stent rings, each stent ring defining a plurality of distal apices; and
  a plurality of connecting members connecting the stent rings,
  wherein the distal apices of the plurality of stent rings are aligned along a first helical direction defining an acute angle relative to the longitudinal axis, the connecting members extending along a second helical direction, the second helical direction being different from the first helical direction and the longitudinal direction,
  wherein each of the stent rings are not in phase or 180 degrees out of phase, and
  wherein the connecting members each include one end connected to a first strut of a first stent ring and a second strut of a second stent ring, wherein the connecting members overlap a larger portion of the first strut of the first stent ring and overlap a smaller portion of the second strut of the second stent ring.

19. A stent including a proximal end and a distal end, the proximal end and the distal end defining a longitudinal direction, the stent comprising:
  a plurality of stent rings, each stent ring defining a plurality of distal apices; and
  a plurality of connecting members connecting the stent rings,
  wherein the distal apices of the plurality of stent rings are aligned along a first helical direction defining an acute angle relative to the longitudinal axis, the connecting members extending along a second helical direction, the second helical direction being different from the first helical direction and the longitudinal direction,
  wherein each of the stent rings are not in phase or 180 degrees out of phase,
  wherein the stent rings each include a plurality of struts connected at their ends to define a zig-zag ring, and,
  wherein the connecting members are connected to some of the plurality of struts at locations offset from their ends and from centers of the struts being connected.

20. A stent comprising:
  a plurality of stent rings expandable from an unexpanded state to an expanded state and each including a plurality of plurality of distal and proximal apices, the plurality of stent rings including a first stent ring having a first middle axis, a second stent ring having a second middle axis a third stent ring adjacent the first stent ring, and a fourth stent ring adjacent the second stent ring;
  a plurality of connecting members for connecting adjacent stent rings at points away from the distal and proximal apices;
  wherein a first connecting member is connected at a first end at a connection point on the first stent ring and is connected at a second end at a connection point on the second stent, a second connecting member is connected at a first end at a connection point on the first stent ring and is connected at a second end at a connection point on the third stent ring, and a third connecting member is connected at a first end at a connection point on the second stent ring and is connected at a second end at a connection point on the fourth stent ring;
  wherein, when the first stent ring is radially expanded the connection points on the first stent ring move toward the first middle axis on the first stent ring and the first and second connecting members move away from the first middle axis resulting in increased spacing between the first stent ring and the third stent ring; and
  wherein, when the second stent is radially expanded, the connection points on the second stent ring move toward the second middle axis on the second stent ring and the third connecting member moves toward the second middle axis resulting in decreased spacing between the second stent ring and the fourth stent ring.

* * * * *